United States Patent [19]

Tsang et al.

[11] Patent Number: 4,923,645

[45] Date of Patent: May 8, 1990

[54] SUSTAINED RELEASE OF ENCAPSULATED MOLECULES

[75] Inventors: Wen-Ghih Tsang, Lexington; Andrew S. Magee, Weston, both of Mass.

[73] Assignee: Damon Biotech, Inc., Needham Heights, Mass.

[21] Appl. No.: 121,214

[22] Filed: Nov. 16, 1987

[51] Int. Cl.$^5$ .......................... A61K 9/62; A61K 9/64; B01J 13/02

[52] U.S. Cl. .................... 264/4.3; 264/4.32; 264/4.33; 424/424; 424/455; 424/457; 424/493; 424/497; 435/178; 514/963

[58] Field of Search ............ 264/4.3, 4.32, 4.33; 424/424, 455, 457, 493, 497; 435/178; 514/963

[56] References Cited

U.S. PATENT DOCUMENTS

| | | | |
|---|---|---|---|
| 3,937,668 | 2/1976 | Zolle | 264/4.3 |
| 3,993,073 | 11/1976 | Zaffaroni | 424/424 |
| 4,205,060 | 5/1980 | Monsimer et al. | 424/495 |
| 4,221,778 | 9/1980 | Raghunathan | 424/483 |
| 4,352,883 | 10/1982 | Lim | 435/178 |
| 4,391,909 | 7/1983 | Lim | 435/178 |
| 4,407,957 | 10/1983 | Lim | 435/178 |
| 4,409,331 | 10/1983 | Lim | 435/178 |
| 4,663,286 | 5/1987 | Tsang et al. | 435/178 |
| 4,690,682 | 9/1987 | Lim | 424/497 |

FOREIGN PATENT DOCUMENTS

| | | | |
|---|---|---|---|
| 0054396 | 6/1982 | European Pat. Off. | |
| 0031991 | 2/1983 | Japan | 435/178 |
| 1163023 | 9/1969 | United Kingdom | 264/4.1 |
| 1414812 | 11/1975 | United Kingdom | |

Primary Examiner—Richard D. Lovering
Attorney, Agent, or Firm—Lahive & Cockfield

[57] ABSTRACT

A method for sustained release of molecules from gels or microcapsules has been developed. The method is based on controlling the gel state using chelating agents or ion transfer. The method is particularly useful for controlling the rate of release of insolubilized proteins into physiological solutions.

13 Claims, 2 Drawing Sheets

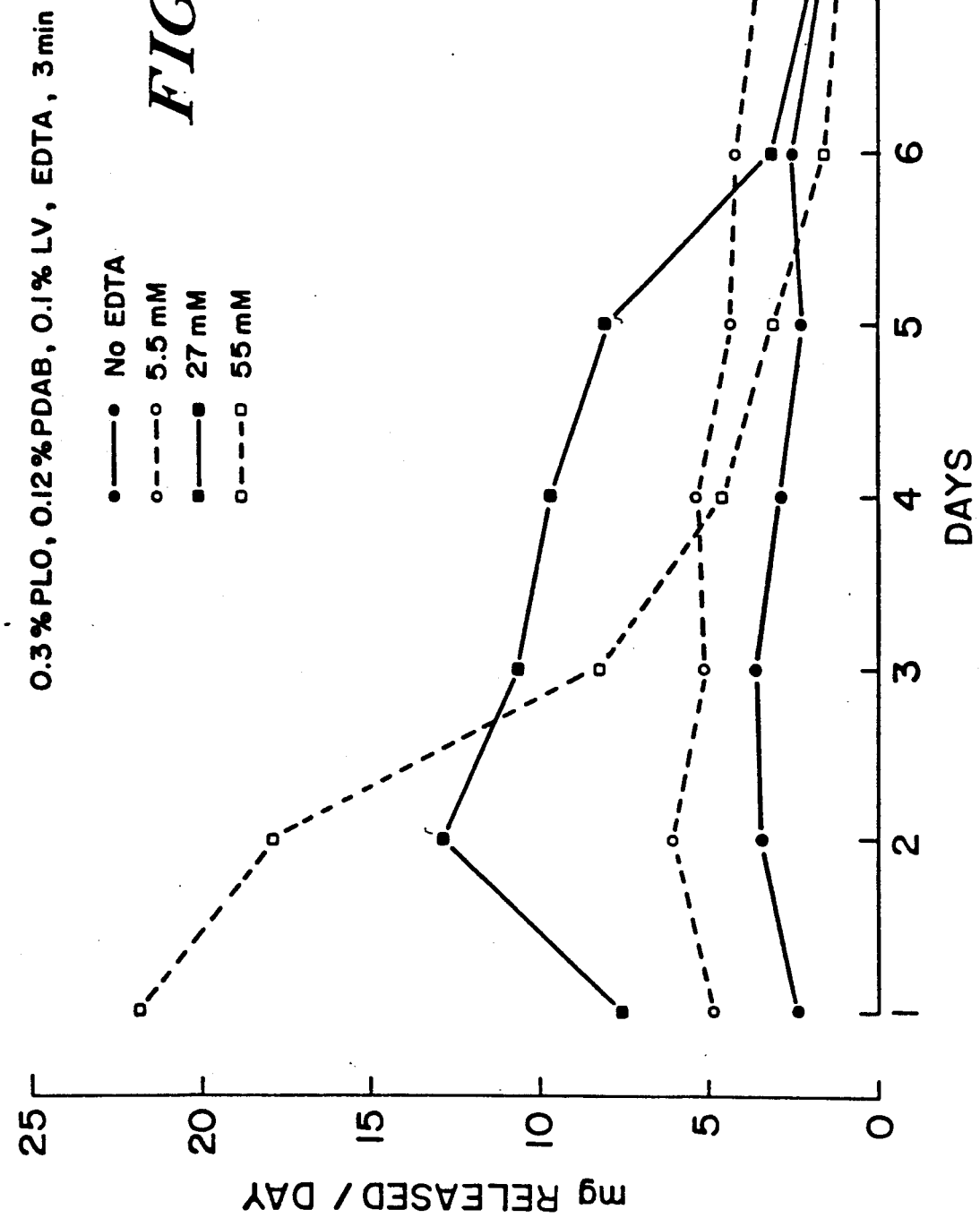

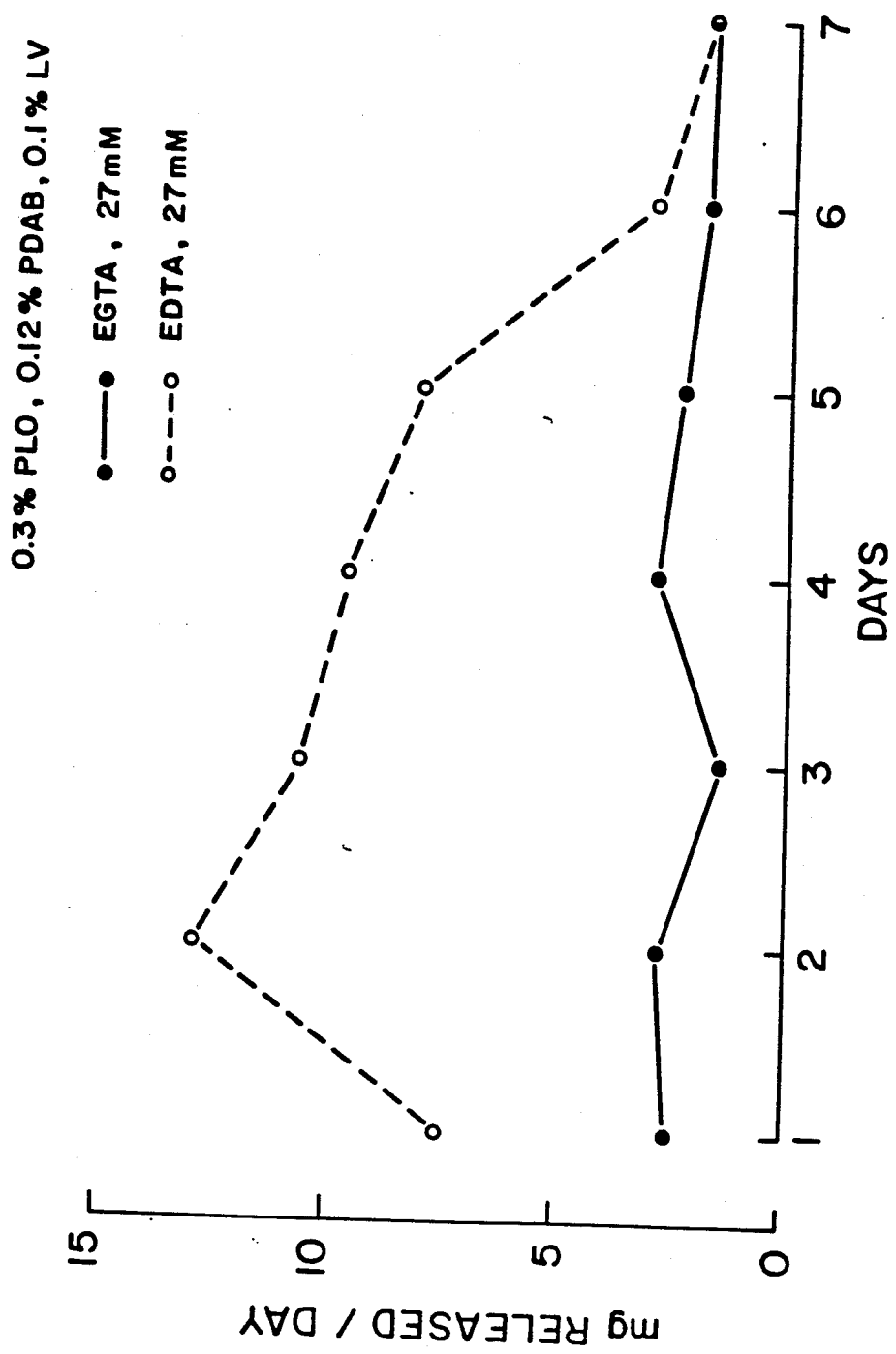

SUSTAINED RELEASE OF ENCAPSULATED MOLECULES

BACKGROUND OF THE INVENTION

The present invention relates to a method for providing sustained release of molecules. More particularly, the invention relates to the release of molecules, e.g., insolubilized proteins, from a reservoir of discrete, implantable gelled masses, with or without surrounding semipermeable membranes.

Incorporation of different core materials within gelled masses, either with or without surrounding semipermeable membranes, has been investigated for a number of years. Much early work involved the use of gelled masses or microcapsules for a variety of testing and storage purposes. However, gelled masses have a tendency to break down over time in physiological solutions. Because of this, some form of membrane is often used to make the gelled masses into a semipermeable capsule. U.S. Pat. No. 4,352,883, issued Oct. 5, 1982, upon application of Dr. Franklin Lim, discloses a basic procedure for encapsulating core materials, including viable cells, within capsules having semipermeable membranes.

Capsules made with the Lim technique may be engineered to have membranes which are permeable to molecules below a particular molecular weight but are substantially impermeable to high molecular weight molecules and to cells. The pores of the membranes are believed to comprise tortuous paths defined by the interstices of the membrane structure. Passage of molecules above a particular molecular weight is hindered by these tortuous path pores, and above a certain higher molecular weight and corresponding larger effective molecular dimensions, the hindrance is sufficiently great that the membrane is substantially impermeable to these molecules.

Porosity control is an important factor in a number of important uses of such microcapsules. For example, the microcapsule membrane can be used for differential screening; that is, to separate molecules on a molecular weight basis. U.S. Pat. No. 4,409,331, issued Oct. 11, 1983, also on an application of Dr. Franklin Lim, discloses a method of differential screening wherein lower molecular weight substances secreted by cells within the capsule may traverse the membrane while other, higher molecular weight materials are confined within the capsules. Such capsules can simplify greatly collection of a substance of interest.

A preferred embodiment of this encapsulation technique involves the formation of shape-retaining gelled masses which contain the core material (the material to be encapsulated) followed by deposition of a membrane on the surface of the gelled masses. The membrane is formed as relatively high molecular weight materials contact the gelled masses and form ionic cross-links with the gel. Lower molecular weight cross-linking polymers permeate further into the structure of the gelled masses, resulting in a reduction of pore size. The duration of membrane formation can also affect pore size since for a given pair of reactants, the longer the gelled masses are exposed to the cross-linking polymer solution, the thicker and less permeable the membrane.

While the techniques for porosity control and membrane formation disclosed in the Lim patent can form acceptable membranes, many applications of capsule technology are better achieved by use of membranes having improved porosity control and better uniformity. The Lim porosity control techniques do not allow fine tuning of the membrane porosity, but rather set rough differential filtering limits.

U.S. Pat. No. 4,663,286, issued May 5, 1987, on application of Dr. Wen-Ghih Tsang et al., discloses modifications and improvements for porosity control on the basic Lim techniques. Gelled masses are formed when a water-soluble polyanionic polymer is gelled by cross-linking with multivalent cations. The gelled masses are expanded, and a more uniform gel ball created, by soaking the gelled masses in an aqueous solution of monovalent cations to remove some of the polyvalent cations. The semipermeable membrane is formed about the expanded gel ball using the basic Lim technique. The improvement in uniformity of the gel balls caused by the soaking step before membrane formation allows more uniform pore size and leads to better porosity control.

In order to obtain release of core material from the capsule without disrupting the capsule membrane, the conventional technique has been to reliquify the unreacted gel by soaking the capsules in a chelating agent that removes the multivalent cations and destroys the cross-linking, thereby dissolving the gel. However, once the capsule interior is reliquified, the only porosity control mechanism is the pore size of the membrane. To obtain sustained release from the interior of the capsule after reliquification, two factors are necessary: the molecule to be released must be smaller then the molecular weight cut-off of the membrane, and there must be a strong osmotic gradient across the membrane driving the released material at a substantially constant rate. U.S. Pat. No. 4,690,682, issued Sept. 1, 1987, on application of Dr. Franklin Lim, discloses such a technique. However, in order to sustain the osmotic gradient, a very large reservoir of the core material must be maintained within the capsule and the core material which has been released must be taken away from the exterior of the capsule at a relatively rapid rate. These limitations may not be feasible.

Accordingly, an object of the invention to provide a mechanism for sustained release of insolubilized molecules into a solution in which they are soluble.

Another object of the invention is to provide a method of controlling the gel state of a gelled ball, either with or without encapsulating within a semipermeable membrane, to facilitate sustained release of molecules encapsulated within the gelled masses.

A further object of the invention is to provide a method of releasing medication in a time-controlled manner.

These and other objects and features will be apparent following description and the drawing.

SUMMARY OF THE INVENTION

The present invention provides a means of controlling the rate of release of molecules, e.g., insolubilized proteins, into a solution in which the molecules are soluble. One use for this type of system is the storage of molecules in an insoluble state followed by time-delayed, steady dosage release into a physiological system in which the molecules are soluble.

The basic method of the invention commences with suspending a molecule, preferably an insolubilized protein, in a solution of a water-soluble polyanionic polymer capable of being gelled by contact with a multivalent cationic cross-linking agent. Preferred water-soluble polyanionic polymers are acidic polysaccharides, most preferably alginate salts. These polyanionic polymers can be gelled by contact with multivalent cations such as calcium to form discrete gelled masses which encapsulate the molecules.

Once the gelled masses are formed, they may either be expanded using a solution of monovalent ions or left unexpanded. In either case, the gel in the gelled masses is deemed to be in a first gel state.

A semipermeable membrane may then be formed about the gelled masses by reaction of the polyanionic material with a polycationic material, e.g,. poly-L-lysine, poly-diamino butyric acid, polyvinyl amine, poly-L-ornithine, or salts thereof. A second membrane can be formed about the first membrane by using a second polycationic material. Post-coating with another, lower concentration solution of a polyanionic material, e.g., alginate, will give an overall negative charge to the capsules, thereby reducing bacterial growth on the capsules.

Once the capsules are formed, or in the case of the gelled masses without membranes, once the gel has been stabilized at the first gel state, the gelled masses or capsules are modified to control the release rate of the insolubilized molecules into a solution in which they are soluble. In one embodiment of the invention, the gelled masses or capsules are treated with a solution of chelating agent which can chelate the multivalent cross-linking agent used for form the original gel. The choice of chelating agent, as well as the concentrations and times of reaction, are selected so that a portion, but not all, of the multivalent cross-linking agent is chelated, effectively removing that portion from the gel. Treatment with the chelating agent leaves the gel in a second gel state, different from the first gel state in terms of gel density and porosity.

A second embodiment of the invention is based on the phenomenon of ionic transfer to modify the gel state. The gelled masses or capsules are treated with a solution of a second multivalent cation different in electropotential from the gelling cation. This second multivalent cation exchanges with the gelling multivalent cation, changing the local charge potential in the gel, resulting in a change in the gel state from the first gel state to a second, different gel state.

The gelled masses or capsules having a gelled interior may be stored or used right away. For use, the gelled masses or capsules are placed in a solution in which the molecule is soluble. This solution will permeate the gel and solubilize the molecule (if insolubilized) inside the gel or capsule interior. The molecule is then released from the capsule or gelled mass by a complex diffusion process. The rate of release of the molecules from the gelled mass or capsule can be either controlled by modifying the concentration of the chelating agent and the length of time that the chelating agent is allowed to react with the gel, or by selection of the second multivalent cation. These means of control are not mutually exclusive and both may be used to fine tune the release rate. These factors will be more clearly illustrated in the following description and examples.

BRIEF DESCRIPTION OF THE DRAWINGS

FIG. 1 is a graph showing the release of an insolubilized protein from capsules which have been treated with four different concentrations of EDTA as a chelating agent; and FIG. 2 is a graph illustrating that selection of different chelating agents can cause different release rates of an insolubilized protein.

DESCRIPTION

The present invention provides a system for sustained release of molecules, preferably insolubilized proteins, into a solution in which the molecules are soluble. The molecules are encapsulated within gelled masses formed of a polyanionic polymer cross-linked with multivalent cationic molecules. A semipermeable membrane may be formed by reacting the gelled masses with a polycationic polymeric molecule. The invention is based, in part, on the recognition that by controlling the gel state of the gelled mass, the release rate of molecules from the interior of the gel can be controlled. Gel state control is achieved by modifying the type, amount and time of reaction of a chelating agent which reacts with the multivalent cross-linking agent, or the type and amount of a second, replacement multivalent cation. In either case, a controlled change is made in the number and strength of cross-links in the gel, thereby accomplishing a corresponding change in gel state, and modifying the rate of release of the encapsulated molecules.

The gel state can also be modified by selection of the proper gel material. For example, alginates differ in the G/M (guluronic/mannuronic) ratio. By using alginates with different G/M ration, the properties of the gel change.

As note previously, the gelled masses are formed of an anionic polymer such as an alginate salt which is cross-linked by a multivalent cation. The gelled masses contain more than 98% water and are essentially soft, shape-retaining balls having a cross-linked gel lattice. Expanding the gelled masses after gelling and before membrane deposition permits better control of the permeability properties and uniformity of the membranes. Immersing the gelled mass in a solution of monovalent cations, e.g., saline, one or more times will remove a portion of the cross-linking polyvalent cations from the gel and increase the hydration state, thereby expanding the gel lattice. Such treatment results in the production of uniformly hydrated gelled masses well suited for the subsequent membrane deposition step. In the absence of such treatment, the gelled masses vary in size and properties because the first formed masses are immersed in the gelling solution longer than the last formed masses. Another important observation is that equilibrating the gelled mass with a solution containing polyvalent cations such as a calcium chloride solution will contract the gelled mass. A further phenomenon which has been discovered is that once a membrane has been formed about a gelled mass, immersion of the capsule in a monovalent cation solution will stretch the membrane, increasing the pore size. These phenomena, coupled with the observation that higher charge density cross-linkers tend to reduce pore size, make it possible to control more precisely the membrane permeability. When these observations are coupled with the permeability control techniques disclosed in the aforementioned patents, there is provided to those skilled in the art a set of parameters which enable production of uniform capsules of consistent and more precise permeability properties. These properties can be modified even more with use of a chelating agent or by cationic exchange.

The chelating agent can be selected from any of the known agents which chelate the multivalent ion used for cross-linking the gel. Proper selection of the chelating agent, as well as the concentration of the agent and duration of treatment, allow control of the release rate. A relatively weak rather than a strong chelating agent is preferred since the strong agent will have a tendency of removing all of the cross-linking multivalent ions, consequently reliquifying the gel, and the sustained release properties of the present invention cannot be obtained once the gel is completely reliquified. If a gel formed of alginate cross-linked by calcium is used as the encapsulating material, chelating agents such as ethylene diamine tetra acetic acid (EDTA), ethylene glycol bis-($\beta$-amino-ethyl-ether)-N, N-tetra-acetic acid (EGTA), or citrate can be used to remove some of the calcium cross-links. If cationic exchange is used to modify the gel state, multivalent ions like $Zn^{++}$ or $Al^{+++}$ can be used to replace the $Ca^{++}$ ions used to form the gel. If ions with a higher electropotential are used, the gel is less porous while if a lower electropotential ion is used, the gel is more porous.

As noted, the present invention may be carried out using gelled masses, or semipermeable membranes may be formed about the gelled masses, forming a more permanent microcapsule. If the gelled masses are used without the capsule membrane, they have the tendency to deteriorate over time, expanding by incorporation additional liquid. However, if a capsule membrane is used, the capsules may be stored for long times without change in properties or effectiveness. This is particularly useful for pharmaceutical compositions.

The gelled masses and/or capsules can be formed using the following procedures.

PROCEDURES

A. Forming the Gelled Masses

As disclosed previously, the core material such as the molecules to be encapsulated e.g., insolubilized proteins, are suspended in a solution containing a water-soluble, reversibly gellable polyanionic polymer, most preferably sodium alginate. The polymer-core material suspension is formed into droplets using conventional means, e.g., a jet-head droplet forming apparatus. The jet-head apparatus consists of a housing having an upper air intake nozzle and an elongate hollow body friction fitted into a stopped. A syringe, e.g., a 10 cc syringe, equipped with a stepping pump is mounted atop the housing with a needle, e.g., a 0.01 inch I.D. Teflon-coated needle, passing through the length of the housing. The interior of the housing is designed such that the tip of the needle is subjected to a constant laminar air-flow which acts as an air knife. In use, the syringe full of the solution containing the material to be encapsulated is mounted atop the housing, and the stepping pump is activated to incrementally force drops of the solution to the top of the needle. Each drop is "cut off" by the air stream and falls approximately 2.5–3.5 cm into a gelling solution where it is immediately gelled by absorption of cross-linking ions. The preferred gelling solution for polyanionic polymers is a calcium ion solution, e.g., 1.2% (w/v) calcium chloride. The distance between the tip of the needle and the cross-linking solution preferably is set to allow the polymer-core material solution to assume the most physically favorable shape, a sphere (maximum volume/surface area). Air within the tube bleeds through an opening in the stopper. The gelled, shape-retaining spheroidal masses preferably are between 50 microns and a few millimeters in diameter and collect in the solution as a separate phase. The gelled masses can be removed by aspiration. For further details of the devices and methods for forming the gelled masses, see U.S. Pat. No. 4,692,284, issued Sept. 8, 1987, on an application of William Braden. This patent, as well as all the other patents cited herein, are assigned to the assignee of the present invention.

The gelled masses may then be expanded by one or more separate immersions or washings in a monovalent cation solution, e.g., saline. This immersion removes a portion of the cross-linking ions, and further hydrates the gel. The gelled masses thus expand to provide better coverage of the core material, the encapsulated molecules, so that the core material does not protrude through the surface of the gel masses. Core material which is anchored to the exterior of the gel is removed by the saline wash. Therefore, only core material in the interior of the gel is encapsulated.

The saline washes also promote more uniform capsule membranes by equilibrating the amount of ionic cross-linking in the polymer lattice of the gel masses. The gelled masses are not all formed simultaneously; the droplets which encounters the cross-linking bath early in the cycle spend a longer time in the bath and therefore retain more ions in the gel structure than those late in the cycle. The saline washes remove more ions from the higher density masses (the early gelled droplets) than from the lesser density gelled masses thereby equilibrating the ionic content of the gelled masses.

B. Membrane Formation

A membrane may then be formed about the expanded gelled mass by reaction between anionic groups on the expended, gelled polymer, and cationic groups on a second polymer. If alginate is used for the capsules, the anionic groups on the alginate can react with cationic groups on a polycationic polymer, e.g., poly-L-lysine or poly-L-ornithine. The polycationic polymer may have a molecular weight as low as 3,000 daltons, but polylysine or polyornithine of 35,000 daltons or higher molecular weight is preferred. After the membrane is formed about the expanded gelled masses, other steps are utilized to fine tune the porosity of the membrane. For example, a series of washes in a saline solutions will expand the pores of the membrane while a series of washes in a calcium chloride solution will contract the pores. A second membrane layer may be formed about the capsules using an additional polycationic polymer, e.g., by exposure to a polyornithine solution or exposure to a higher charged density polymer such as polyvinyl amine. This technique may be used to decrease pore size.

Post-coating the capsules with a solution of a polyanionic polymer, e.g., sodium alginate, substantially removes the tendency for the capsules to clump. The anionic polymer reacts with residual cationic sites on the membrane causing negative surface polarity. As is known in the prior art, negative surfaces may inhibit growth and attachment of cells. Such growth can hinder intracapsular call growth or adversely affect permeability. Additionally, immersing the capsule in a neutralizing agent such as 2-N-cyclohexylamino ethan sulfonic acid (CHES) or other zwitterion buffer may reduce the reactivity of and improve the capsule membrane.

C. Altering the Release Characteristics

EXAMPLE 1.

Gelled masses were made using 9 ml of a 1.4% solution (W/V) sodium alginate (NaG-Kelco LV) containing 450 mg of insolubilized protein. The jet-head apparatus, as previously described, was used to form droplets by forcing the suspension through a 22 gauge needle at a rate of approximately 5 ml per minute. The droplets fell approximately 3 cm into 120 ml of a 1.2% (W/V) calcium chloride solution, forming gelled masses which were collected by aspiration. Approximately 1.5 to 1.8 ml of settled gelled masses were used for each sample. Each sample contained approximately 75 mg of the insolubilized protein. The gelled masses contacted with physiological saline, two changes, for a total of approximately eleven minutes.

The gelled masses, without a membrane, were then immersed in 3 mM sodium citrate for two, three or four minutes. The final volume of the expanded gelled masses was approximately 2 ml per sample. The gelled masses were then placed in a Tris buffer, pH 7.4, with 0.02% Na azide added, and the buffer was tested each day for protein content by UV absorbance at 280 nm. Table 1 gives the results of this testing.

TABLE 1

| DAY | A (mg/ml) | B (mg/ml) | C (mg/ml) | D (mg/ml) |
|-----|-----------|-----------|-----------|-----------|
| 1   | 0.113     | .471      | .445      | .508      |
| 2   | 0.076     | .323      | .285      | .512      |
| 3   | 0.126     | .127      | .327      | .331      |
| 4   | 0.208     | .236      | .304      | .311      |
| 5   | 0.175     | .368      | .389      | .351      |
| 6   | 0.191     | .344      | .400      | .376      |
| 7   | 0.337     | .461      | .497      | .394      |
| 8   | 0.377     | .619      | .534      | .544      |
| 9   | 0.018     | .656      | .839      | .555      |
| 10  | 0.152     | .236      | .135      | .450      |

Column A, the control, was not treated with citrate while Column B was treated for two minutes, Column C for three minutes, and Column D for four minutes. All values are in mg/ml of protein recovered from the buffer after the 24 hour period. As can be seen, treating with the sodium citrate clearly speeds the rate of release of the insolubilized protein from the gelled masses.

EXAMPLE 2.

In this Example, the effect of the chelating agent EDTA on the release of the insolubilized protein from capsules having a semipermeable membrane was investigated. The gelled balls were made and treated as explained in Example 1 through the stage of saline treatment. After the saline treatment, a semipermeable membrane was formed by contacting the gelled masses with a 0.3% solution of poly-L-ornithine (Damon Biotech, Inc., 50,000 dalton molecular weight) in isotonic saline solution. After fourteen minutes of reaction, the resulting capsules were washed for ten minutes with a 0.3% solution of PIPES buffer (Sigma). The capsules were washed approximately eight minutes with physiological saline, and a second membrane was formed about the capsules by a ten minute reaction with 0.12% polydiamino butyric acid. The capsules were washed again with isotonic saline and post-coated with a three minute immersion in 0.% sodium alginate (NaG-Kelco LV). The capsules were washed twice in saline then immersed in a solution of the chelating agent. Four different samples were treated in this manner: the control had no EDTA treatment and the remaining samples were treated with 5.5 mM, 27 mM, and 55 mM EDTA, respectively. The capsules were then washed again with saline and placed in Tris buffer, pH 7.4, and the buffer was tested daily for protein.

FIG. 1 shows the results of this experiment. This Figure is a plot of mg protein released/day versus time. As is evident from the Figure, the higher concentration of chelating agent used, the faster the initial release rate of protein from the capsules. However, a more controlled release was obtained by using a lower concentration of chelating agent. Even this lower concentration, however, yielded a faster release rate than was obtained from the untreated capsule. This clearly demonstrates that modifying the concentration of the chelating agent can control the release rate of insolubilized protein from a capsule.

EXAMPLE 3.

In this Example, two different chelating agents, EDTA and EGTA, were compared, at the same concentration, to see what the effect would be on release rate. Capsules were manufactured in the manner described in Example 2 except one sample was treated with 27 mM EGTA for three minutes while the other was treated 27 mM EDTA for three minutes.

FIG. 2 shows the results of this experiment. This Figure is also a plot of mg protein released/day versus time. As expected from the results of Example 2, the EDTA capsules showed a much faster release rate then did the EGTA capsules. The EDTA is a much stronger chelating agent than the EGTA, and more calcium ions are chelated in the same time for equal concentrations of the EDTA than EGTA. Accordingly, the gel within the capsules is more "liquid" if EDTA is used as a chelating agent and a faster release rate is expected.

As shown by these Examples, controlled release rate of an insolubilized protein from a microcapsule or gelled mass can be controlled by varying concentration, length of time of treatment, and selection of chelating agent. Varying these factors modifies the gel state and can lead to a means of controlled sustained release for drug or other delivery systems over time. Replacing the ions in the gel with ions of different electropotential can accomplish the same purpose.

Those skilled in the art may discover other embodiments of the invention without departing from the scope thereof. Such further embodiments are considered within the scope of the following claims.

What is claimed is:

1. A method of providing controlled release of molecules encapsulated in a gelled mass with a surrounding semi-permeable membrane into a solution in which said molecules are soluble, the method comprising the steps of:
   A. suspending said molecules in a solution of a polyanionic polymer which can be reversibly gelled by contact with a chelatable, multivalent cationic cross-linking agent;
   B. gelling said polyanionic polymer by contacting said polymer with said multivalent cationic cross-linking agent to form a gelled mass with said molecules encapsulated therein;
   C. forming a semi-permeable membrane about said gelled mass by contacting said gelled mass with a solution of a polycationic polymer, said gelled mass within said semi-permeable membrane being in a first semi-solid gel state;

D. controlling the release rate of said encapsulated molecules into said solution in which they are soluble by modifying the gel state of the gelled mass within said semi-permeable membrane from said first semi-solid gel state to a second semi-solid gel state by treating said gelled mass for a predetermined duration with a solution containing a predetermined concentration of a chelating agent, said treatment resulting in reversibly controlled modification of the gel state of said gelled mass without liquification of said gelled mass or disruption of said semi-permeable membrane, said release rate of said molecules being different from said gelled mass when in said first gel state than it is in said second gel state.

2. The method of claim 1 wherein said encapsulated molecules comprises insolubilized molecules which are insoluble at the conditions of encapsulation.

3. The method of claim 1 wherein said gelled mass are expanded by treating with a solution of univalent cations before treatment with said chelating agent, and said first semi-solid gel state comprises the state of said gel after expansion.

4. The method of claim 1 wherein said polyanionic material comprises alginate.

5. The method of claim 4 wherein said multivalent cationic cross-linking agent comprises calcium ions.

6. The method of claim 5 wherein aid chelating agent is selected from a group consisting of EDTA, EGTA, citrate, and salts thereof.

7. The method of claim 1 wherein said polycationic polymer selected from a group consisting pf polylysine, polyornithine, poly-diamino butyric acid, polyvinyl amine, and salts thereof.

8. A method of providing controlled release of molecules encapsulated in a gelled mass with a surrounding semi-permeable membrane into a solution in which said molecules are soluble, the method comprising the steps of:

A. suspending said molecules in a solution of a polyanionic polymer which can be reversibly gelled by contact with a first multivalent cationic cross-linking agent;

B. gelling said polyanionic polymer by contacting said polymer with said first multivalent cationic cross-linking agent to form a gelled mass with said molecules encapsulated therein;

C. forming a semi-permeable membrane about said gelled mass by contacting said gelled mass with a solution of a polycationic polymer, said gelled mass within said semi-permeable membrane being a first semi-solid gel state;

D. controlling the release rate of said encapsulated molecules into said solution in which they are soluble by modifying the gel state of the gelled mass within said semi-permeable membrane from said first semi-solid gel state to a second semi-solid gel state by treating said gelled mass for a predetermined duration with a solution containing a predetermined concentration of a second multivalent cationic cross-linking agent of a different electropotential than said first multivalent cationic cross-linking agent, said treatment resulting in reversibly controlled modification of the gel state of said gelled mass without liquification of said gelled mass or disruption of said semi-permeable membrane, said release rate of said molecules being different from said gelled mass when in said first gel state than it is in said second gel state.

9. The method of claim 8 wherein said encapsulated molecules comprise insolubilized molecules which are insoluble at the conditions of encapsulation.

10. The method of claim 8 wherein said polyanionic material comprises alginate.

11. The method of claim 10 wherein said first multivalent cation cross-linking agent comprises calcium ions.

12. The method of claim 11 wherein said second multivalent cationic cross-linking agent is selected from a group consisting of zinc and aluminum ions.

13. The method of claim 8 wherein said polycationic polymer is selected from a group consisting of polylysine, polyornithine, poly-diamino butyric acid, polyvinylamine, and salts thereof.

* * * * *